United States Patent

Pappas

[19]

[11] Patent Number: 5,824,101
[45] Date of Patent: Oct. 20, 1998

[54] PROSTHESIS WITH ARTICULATING SURFACE STRESS REDUCING CONTACT EDGE

[75] Inventor: Michael J. Pappas, Caldwell, N.J.

[73] Assignee: Biomedical Engineering Trust I, N.J.

[21] Appl. No.: 914,126

[22] Filed: Aug. 19, 1997

Related U.S. Application Data

[63] Continuation-in-part of Ser. No. 345,302, Nov. 28, 1994, Pat. No. 5,683,467.

[51] Int. Cl.$^6$ ....................................................... A61F 2/38
[52] U.S. Cl. .................................................................. 623/20
[58] Field of Search ........................................... 623/18–23

[56] References Cited

U.S. PATENT DOCUMENTS

| | | |
|---|---|---|
| 3,715,763 | 2/1973 | Link . |
| 4,081,866 | 4/1978 | Upshaw et al. . |
| 4,183,104 | 1/1980 | Frey . |
| 4,470,158 | 9/1984 | Pappas et al. . |
| 4,586,933 | 5/1986 | Shoji et al. . |
| 5,021,061 | 6/1991 | Wevers et al. . |
| 5,152,799 | 10/1992 | Lyons . |
| 5,358,530 | 10/1994 | Hodoreck . |
| 5,387,240 | 2/1995 | Pottenger et al. . |
| 5,395,401 | 3/1995 | Bahler . |
| 5,489,311 | 2/1996 | Cipolletti . |

FOREIGN PATENT DOCUMENTS

| | | |
|---|---|---|
| 0 226 762 | 7/1987 | European Pat. Off. . |
| 0 302 850 | 2/1989 | European Pat. Off. . |
| 0415 761 | 3/1991 | European Pat. Off. . |
| 0 600 806 | 6/1994 | European Pat. Off. . |
| 0 716 838 | 6/1996 | European Pat. Off. . |
| 2 634 373 | 1/1990 | France . |
| G 91 10 504.8 | 12/1991 | Germany . |

OTHER PUBLICATIONS

European Search Report dated Apr. 16, 1996 for European Patent Appl. No. 95118660.0.
Pappas, et al. "Contact Stresses in Metal–Plastic Total Knee Replacements: A Theoretical and Experimental Study", Jan. 23, 1986, pp. 1–7.

*Primary Examiner*—Michael J. Milano
*Attorney, Agent, or Firm*—Anthony J. Casella; Gerald E. Hespos; Ludomir A. Budzyn

[57] ABSTRACT

A prosthesis tibial bearing of thermoplastic material has a planar surface which engages the mating planar surface of a second prosthesis component such as the tibial platform. The typically metal platform edge wipes across the inner surface region of the bearing causing deformation of the bearing surface. This deformation causes stress magnification in the bearing at the platform edge region. The edge region of the platform planar surface is tapered to provide a gradual curved ramp between a relatively small corner radius at the platform edge and the platform planar surface, the tapered region being tangential to the edge radius and to the platform planar surface. The stress concentration increase at the edge region of the bearing is reduced at the platform edge region to below 100% and preferably to about 25% of the stress value between the bearing and the platform in the region interior the platform edge. The tapered surface region is preferably a curvature of tangential contiguous radii tangent to the platform planar surface, but may be planar.

24 Claims, 10 Drawing Sheets

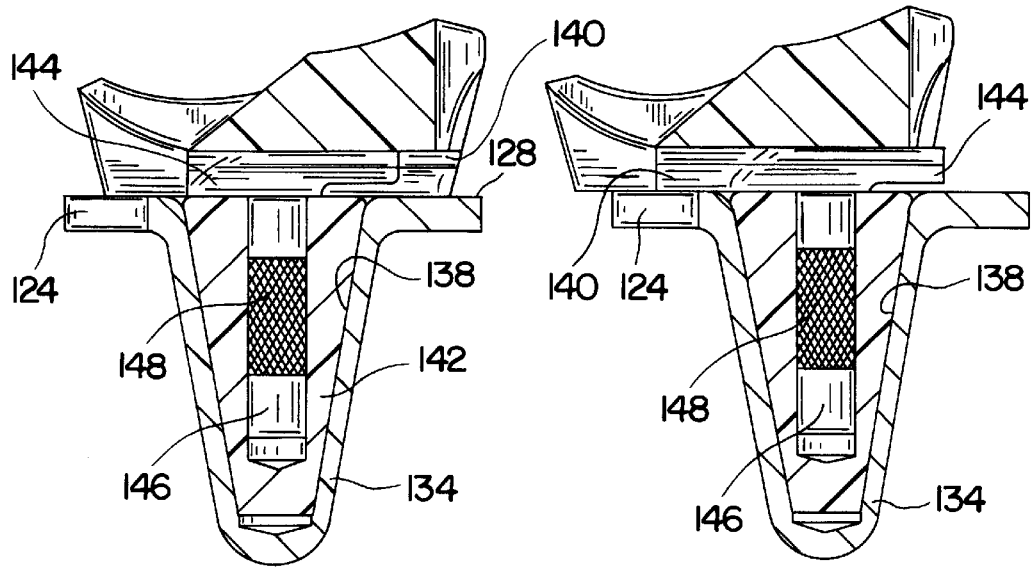
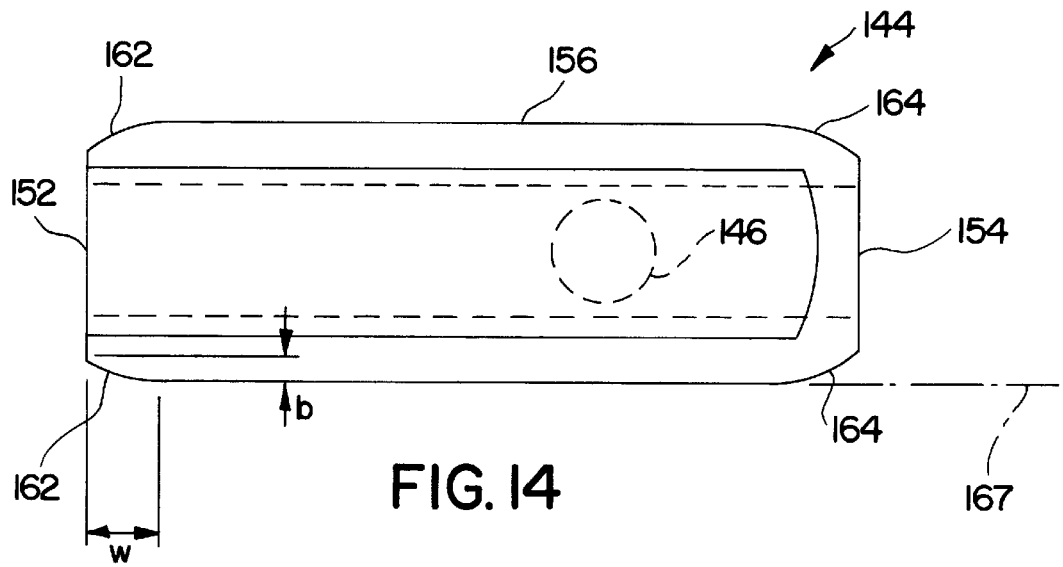
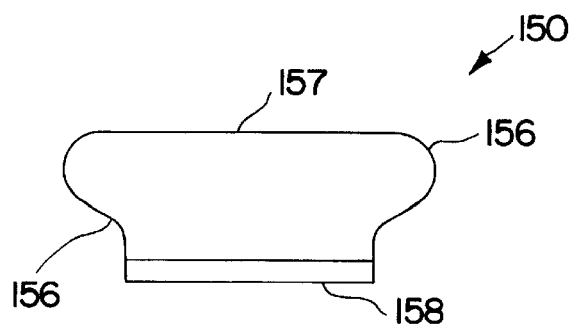

PROSTHESIS WITH ARTICULATING SURFACE STRESS REDUCING CONTACT EDGE

This application is a continuation-in-part of Ser. No. 08/345,302, filed Nov. 28, 1994 now U.S. Pat. No. 5,683, 467.

BACKGROUND OF THE INVENTION

1. Field of the Invention

This invention relates to prostheses with two or more prosthetic components that have surfaces which articulate, slide or otherwise move such that an edge of the surface of one component engages the surface of the mating component.

2. Description of the Prior Art

Frequently in the articulation surfaces of artificial human or animal joints an edge of one surface will move across another surface (referred to herein as "edge wiping"). This occurs, for example, in a hip replacement joint where the truncation of the femoral head spherical surface produces an edge that wipes at least part of the articulating surface of the ultra high molecular weight polyethylene (UHMWPe) acetabular bearing. Another example includes a prosthesis in which the edge of an articulating surface of a metallic acetabular component wipes over the surface of a plastic femoral head.

The present inventor has observed and recognizes that where a surface edge of a first articulating surface of an articulating prosthesis couple contacts an interior region of the second articulating surface of the couple, the compressive load in the second surface changes suddenly as the second surface loses contact with the first surface. This is because the compressive load produces deformation, i.e., strain, of at least one of the mating surfaces. But such strain can occur also with plastic to plastic contact and with metal to metal contact. The deformation terminates abruptly at the edge region of one surface of the couple where the edge region overlies an interior region of the other couple surface.

This sudden change in strain in the interior of the other couple surface produces a stress riser (stress magnification) in the prothesis material in the region of the edge contact. This is illustrated in FIG. 1. In FIG. 1, a representative prior art metallic-plastic articulating couple formed by prosthesis 1 is illustrated showing a prosthesis thermoplastic bearing 2 having a first surface 3 engaged with a second surface 5 of metal platform 4. When the bearing 2 exerts a compressive load on the platform 4, in direction 7, the stress contour curve 8 is generally uniform as shown in region 11 except for the edge region 6. The stress in edge region 6 is significantly higher than the stress in interior region 11, generally about a 400% increase in stress in the material, due to the abrupt change in strain 6 in the edge region 6.

When the first surface 3 is metallic, this local increase in stress is not as important since the metallic surface is strong enough to endure this large increase in stress in a prosthesis environment without significant damage. In a prosthesis environment the motions between the articulating surfaces are relatively slow and the stresses negligible in comparison to the metal material strength properties. This results in negligible damage to the surfaces.

When, however, a metallic edge 9, such as on platform 4, wipes a surface of a thermoplastic member, such as surface 3 of bearing 2, a localized strain 6 is produced which varies to a maximum relatively abruptly and which strain produces the stress increase at curve portion 10 in region 6. This stress increase portion 10 will usually produce greatly increased thermoplastic surface 3 damage in joint replacement articulations as the edge 9 of the one surface such as the surface 5 of platform 4 wipes over the mating surface such as surface 3 of bearing 2.

In contrast to the above analysis of the present inventor, those of ordinary skill in prosthesis design concluded differently in the observation of damage resulting in the plastic bearings of replacement joints where a plastic head is used with a metallic socket in which the edge of the socket wipes the surface of the plastic head. It is of general belief by those of ordinary skill in this art that the concave element of an articulating plastic-metal couple must be plastic, and the convex element must be metallic.

However, as observed by the present inventor as discussed above, the problem of surface damage of the thermoplastic component is not directly related to the issue of concavity or convexity. For example, if the articulation is incongruent, and there is no edge wiping effect, whether the convex surface is metallic or plastic does not substantially affect the maximum contact stress in the plastic. Often with incongruent contact, it is desirable to make the head of plastic and the socket of metal since, during articulation, the damaging peak loads would be spread over a larger plastic surface reducing the damaging effect of these loads on the plastic.

The present inventor was involved in the development of a shoulder prosthesis with a plastic head which was in incongruent contact with a metallic socket, a configuration which is superior to a similar design with a metallic head and a plastic socket. Yet the perception by those of ordinary skill in this art that the convex articulating surface element must be metallic was, and is, so pervasive that the device could not, and cannot today, be brought to market. Thus the edge wiping phenomenon as discussed above is not generally understood by those of ordinary skill in the prosthetic design art.

SUMMARY OF THE INVENTION

The utilization of the principle of edge strain/stress and resulting deformation and damage to an articulating surface according to an embodiment of the present invention provides an arrangement of articulating surfaces of a prosthesis couple which takes into consideration the edge wiping effect providing an improved prosthesis.

In a prosthesis including a joint comprising first and second members each having a surface thereof articulating under load in contact with one another, the combination according to the present invention comprises a first member having a first surface and a second member having a second surface for engaging in articulating contact the first surface, the second surface having an edge, the second surface including the edge being under compressive load with the first surface during the articulating contact, the compressive load causing the first member in the region of the second surface to exhibit a contact stress of generally a first value, the second surface having a gradual tapering region adjacent to and extending inwardly the second surface from the second surface edge a distance W so as to cause the first member to exhibit increased edge stress concentration in the region of engagement of the edge of the second surface with the first surface of a second value in the first member of no more than about twice the first value. As a result of the reduced edge stress concentration, the edge wiping generates a minimum of damage to the first surface especially when the first surface is of lower strength than the second surface.

In one embodiment, the second member is metal and the first member is a thermoplastic.

In a further embodiment the increased edge contact stress second value is about 25% greater than the first value.

In a prosthesis including a joint comprising first and second members each having a surface thereof articulating under load in contact with one another in accordance with a further embodiment, the combination comprises a thermoplastic first member having a first surface and a second metallic member having a second surface for engaging in articulating contact the first surface, the second surface having an edge, the second surface including the edge being under compressive load with the first surface during the articulating contact, the second surface having a gradual tapering region adjacent to and extending inwardly the second surface from the edge a distance W so as to cause the first member to exhibit a gradual preferably uniform rate of change of deformation in the first surface in response to the compressive load with the second surface such that the deformation varies from essentially zero at the edge to a maximum at the planar second surface the distance W.

The subject invention is not only limited to edge stress concentrations generated between articulating surfaces. In particular, the principles of the subject invention may be employed in other prosthetic joints where an edge of one prosthetic component slides in proximity to a corresponding region on an adjacent prosthetic component. For example, the stress reducing contact edge of the subject invention may be employed where an elongate guide element of one prosthetic component is slidably received in a slot of another prosthetic component. At certain ranges of movement of the guide element in the slot, edge wiping may occur. One of the two elements in such a prosthetic joint is likely to be metallic and the other is likely to be a thermoplastic material to avoid rubbing or sliding contact between similar materials. In these situations, the wiping of a metallic edge of, for example, the guide element along a surface of the thermoplastic element defining the slot can create the above-described stress concentrations that can lead to premature failure of the thermoplastic component. To avoid these problems, regions of the prosthetic component adjacent the edge may be relieved or cammed as described above to prevent stress concentrations and associated premature failure. In this embodiment, as explained further below, the prosthetic component formed with the stress reducing contact edge is not truly an articulating surface and is not planar.

BRIEF DESCRIPTION OF THE DRAWINGS

FIG. 12 is a cross-sectional view of the assembled prosthesis taken along line 3—3 and showing the prosthesis during extension of the knee joint.

FIG. 13 is a cross-sectional view similar to FIG. 12, but showing the knee joint in flexion.

FIG. 14 is a top plan view of the control arm shown in FIGS. 10–13.

FIG. 15 is a front elevational view of the dove-tailed portion of the control arm.

DETAILED DESCRIPTION OF THE PREFERRED EMBODIMENTS

Figure 2:
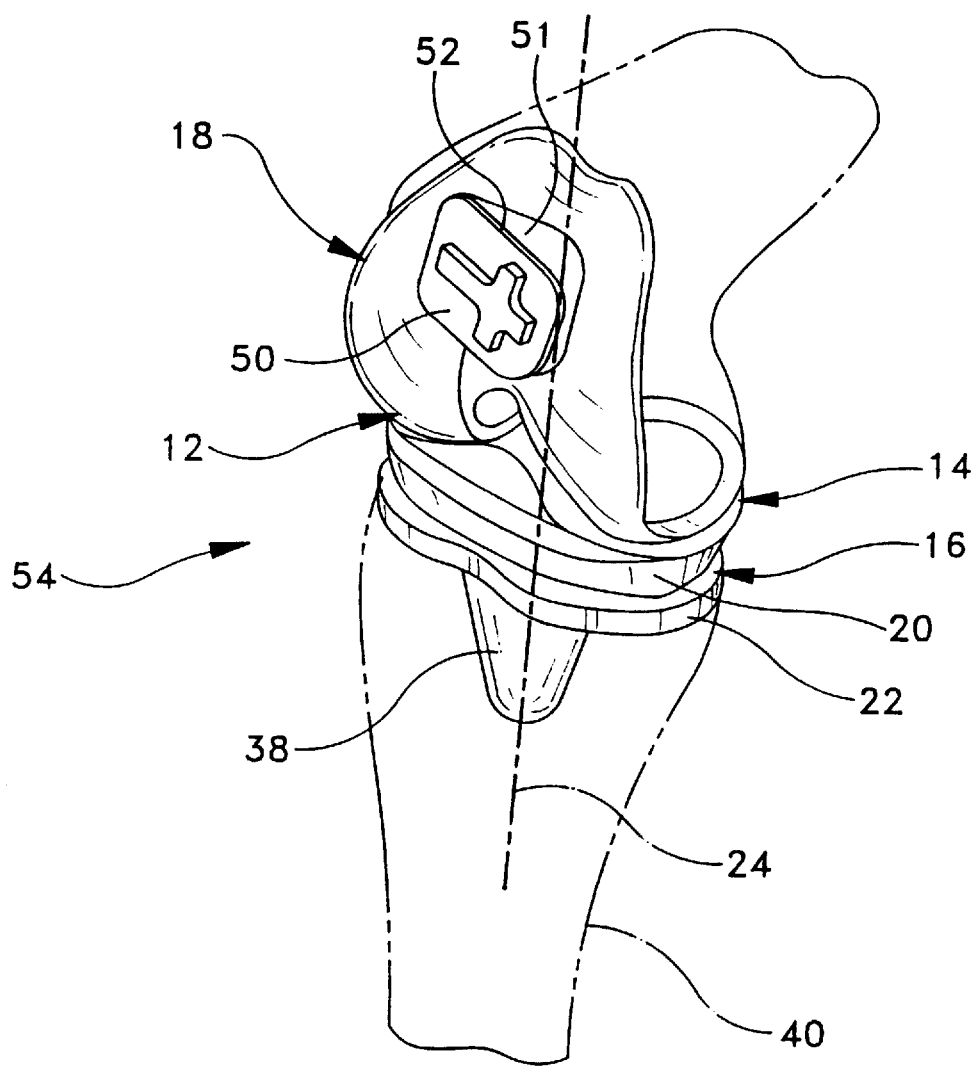
FIG. 2 is an isometric view of a knee and prosthesis embodying the present invention.

A knee replacement incorporating the subject invention is identified generally by the numeral 12 in FIG. 2. The knee replacement 12 is generally of known construction, except for the improvement to be described below. Therefore the details of the various components forming replacement are not given herein. The replacement 12 comprises a femoral component 14, a tibial component 16 and a patellar component 18. The tibial component 16 comprises a tibial bearing 20 and a tibial platform 22 which are rotatable with respect to each other about an axis 24.

Figure 3:
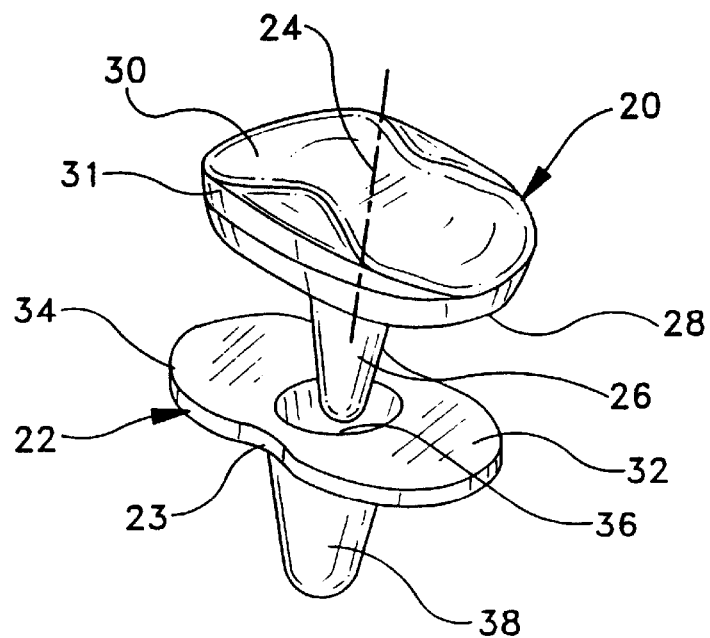
FIGS. 3 and 4 are respective exploded and assembled isometric views of a bearing and platform assembly portion of the embodiment of FIG. 2.

The bearing 20 is formed from ultra high molecular weight polyethylene (UHMWPe), and includes a depending conical stem 26 as shown in FIG. 3. The bearing 20 has a planar surface 28 for engaging a mating planar surface 32 of the tibial platform 22 and a bearing surface 30 for receiving the mating condyle of the femoral component 14. The bearing 20 also has a peripheral edge 31.

The tibial platform 22, may be formed from a metal material known in this art, and includes a platform member 23 which has planar platform surface 32. The surface 32 of the platform member 23 has a peripheral edge 34. The platform 22 has a conical cavity 36 within conical stem 38 which is implanted in the tibia 40 as shown in FIG. 2. The cavity 36 receives the stem 26 of the bearing 20 along axis 24 defined by the cavity 36 and the stem 26. The bearing 20 rotates about axis 24 relative to the platform 22 via the engaged conical tibial stem 26 and platform cavity 36. The bearing surface 28 compressively engages the platform surface 32 during this rotation.

Figure 4:
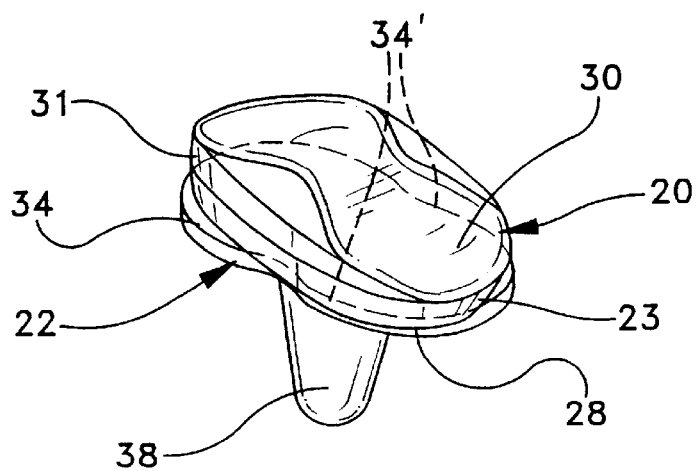

The edges 31 of the bearing and 34 of the platform are irregular, elongated and somewhat oval in plan view. Rotation of the bearing 20 about axis 24 with respect to platform 22 results in the edge 34 portions 34' of the platform 22 engaging and overlying corresponding interior portions of the planar surface 28 of the bearing 20, as shown in FIG. 4.

Compressive loads between the tibial bearing 20 an tibial platform 22 during articulation are borne by the engaged planar tibial bearing surface 28 and the planar tibial platform surface 32. During normal human activity, rotation of the tibial bearing 20 relative to the tibial platform 22 about axis 24 may result in the edge 31 of the tibial bearing 20 overhanging the edge 34 of the tibial platform 22, as shown in FIG. 4. Also, the edge 34' of the platform may overlie the bearing surface 28. Such motion will produce an edge wiping effect and increase wear on the tibial bearing surface 28 if the tibial platform edge 34 were made in the conventional manner of FIG. 1.

Figure 1:
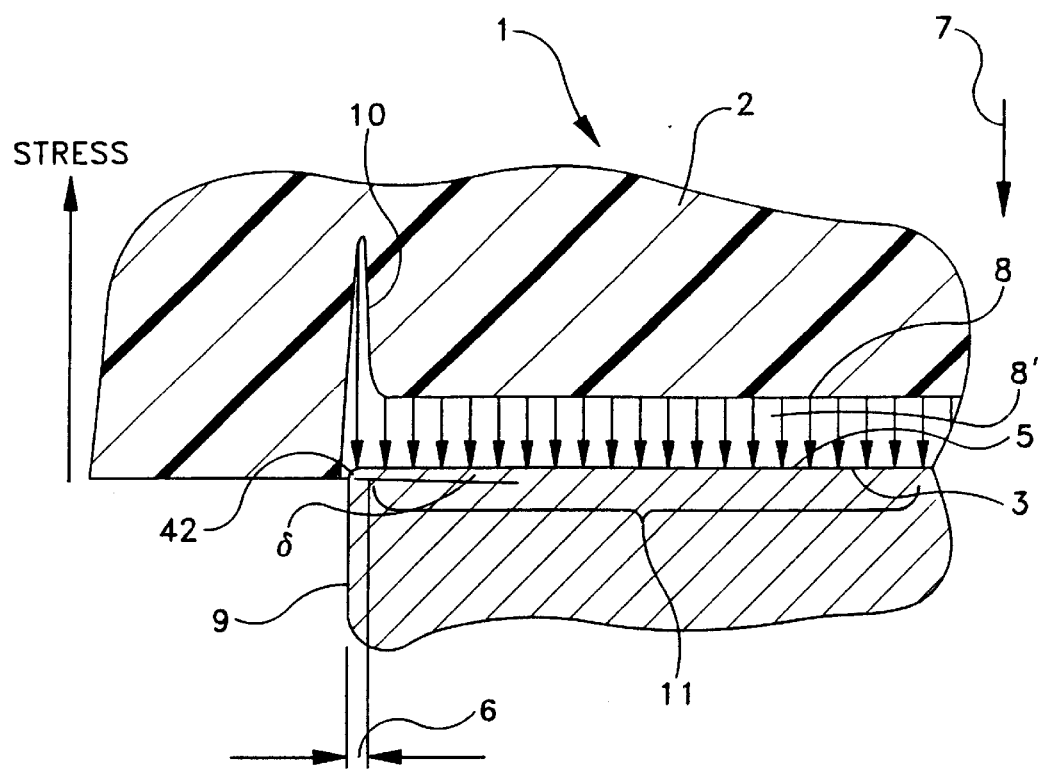
FIG. 1 is an illustration of prior art prosthesis components in contact with each other including a stress contour graph useful for explaining the edge stress principles.

In FIG. 1, the corner of the metallic edge 9 of the platform 4 adjacent to the surface 3 of the bearing 2 has a relatively small radius 42. The relatively small radius 42 which is typically about 0.7 mm results in the compression stress contour 8 as discussed in the introductory portion. The increased stress concentration curve portion 10 at the region 6 of radius 42 is undesirable. This stress may have a magnitude of about 400% the stress magnitude of the uniform portion 8' region 11 of the stress contour curve 8. The abrupt change in deformation (strain) δ of the bearing 2 at the edge 9 causes undue wear of the bearing 2 as the platform 4 rotates on the bearing planar surface 3. Surface 3 is no longer planar at the edge region of radius 42 due to the deformation δ in the softer thermoplastic bearing 2.

Figure 8:
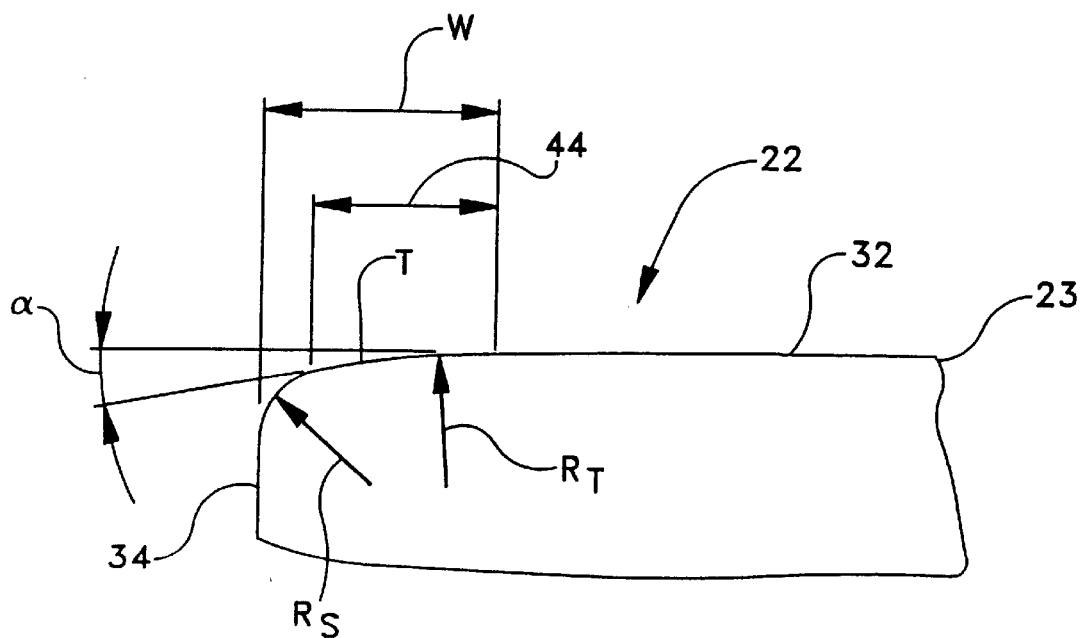
FIG. 8 is a side elevation sectional view of the platform of FIG. 5 useful for explaining further principles of the present invention.

With reference to FIG. 8, an embodiment of the present invention includes planar tibial platform member 23 with a surface 32 that has a tapered region 44 extending inwardly from a small radius $R_s$ adjacent the edge 34. As in the prior art described above, the radius $R_s$ may typically be about 0.7 mm. The region 44 is inclined relative to the planar surface 32 of the platform 23 generally less than 10° and preferably considerably smaller. For example, the region 44 may extend inwardly from edge 34 a distance W which may be about 3.2 mm in one embodiment. In this embodiment the region 44 is defined by a relatively larger radius $R_t$, which may be about 50 mm.

The tapered surface T in region 44 is tangent to planar surface 32 and to the radius $R_s$ in this embodiment. In this case the angle α of surface T to the plane of surface 32 is much smaller than 10°. The width W and inclination of the tapered surface T may differ according to a given implementation. The width W and angle α may be determined empirically for a given implementation to minimize the undesirable edge wiping wear discussed above. The factors to consider are relative hardness of the two engaging surfaces and the anticipated load.

UHMWPe bearing material and typical metals employed for prosthesis components such as a cobalt chromium alloy or a ceramic coated titanium alloy are employed in the present embodiment. Surface finishes are highly polished and smooth as in typical for such components as used in the prior art and thus are not a major factor in the edge stress condition. The load in the typical prosthesis is assumed for normal human implementations and, therefore, is also not a major factor from prosthesis to prosthesis design. Also, the tapered surface T may be curved or planar, a curve being preferable. The curvature of the curve does not necessarily have to be formed by a single radius and a non-circular curve is preferred. Such a curve gradually slopes and merges into surface 32 tangentially and then increases in inclination relative to surface 32 as it tangentially approaches the radius $R_s$. Such a curve might be hyperbolic or a similar curve. In this case the angle α is only a generalized average value of the curved surface T.

Figure 5:
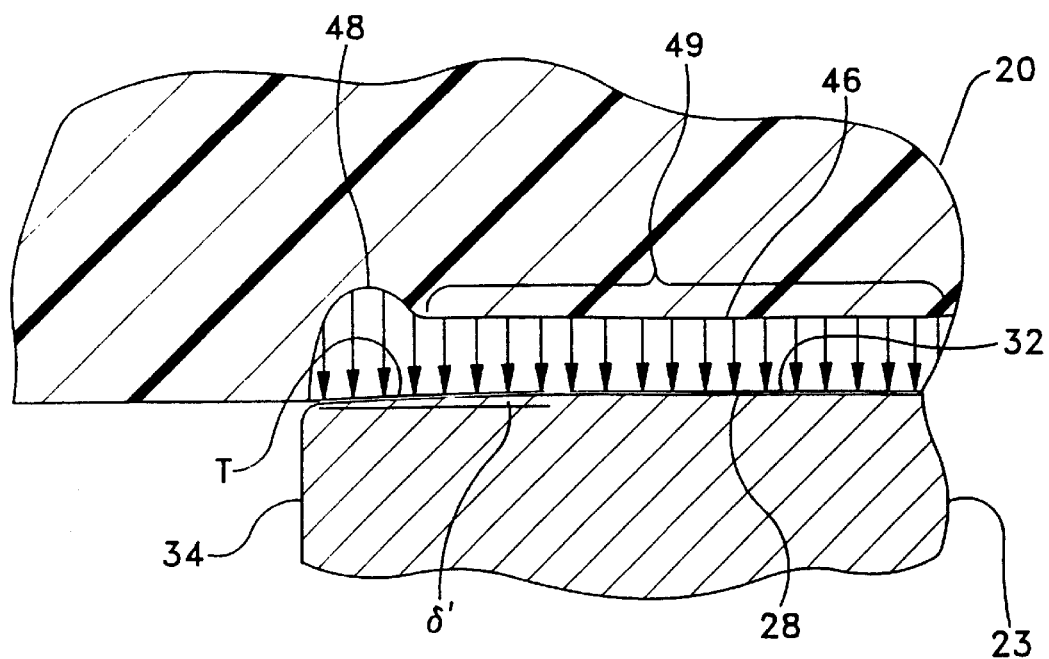
FIG. 5 is an illustration of prosthesis components according to an embodiment of the present invention useful for explaining some of the principles of the present invention.

FIG. 5 illustrates a stress curve 46 having a stress concentration portion 48 for the platform member 23 and bearing 20. Region 49 has a substantially uniform stress as represented by the horizontal line portion of curve 46 parallel to surface 32. The tapered surface T produces a maximum deformation δ' in the bearing 20 which deformation is not abrupt at the area adjacent the edge 34 as occurs in the prior art of FIG. 1. It should be understood that the drawing is not to scale and the actual inclination of tapered surface T is much less than that illustrated, which inclination is exaggerated for purposes of illustration. The deformation δ' is gradual and tapers slightly from essentially a minimum or negligible value at the end 34 to the maximum value in the interior region 49 of platform 23 surface 32 and bearing 20 surface 28 a distance W (FIG. 8). The stress concentration in the region of curve portion 48 of curve 46 is a maximum of about 25% greater than the average value of the stress in the remaining portion of curve 46.

Figure 9:
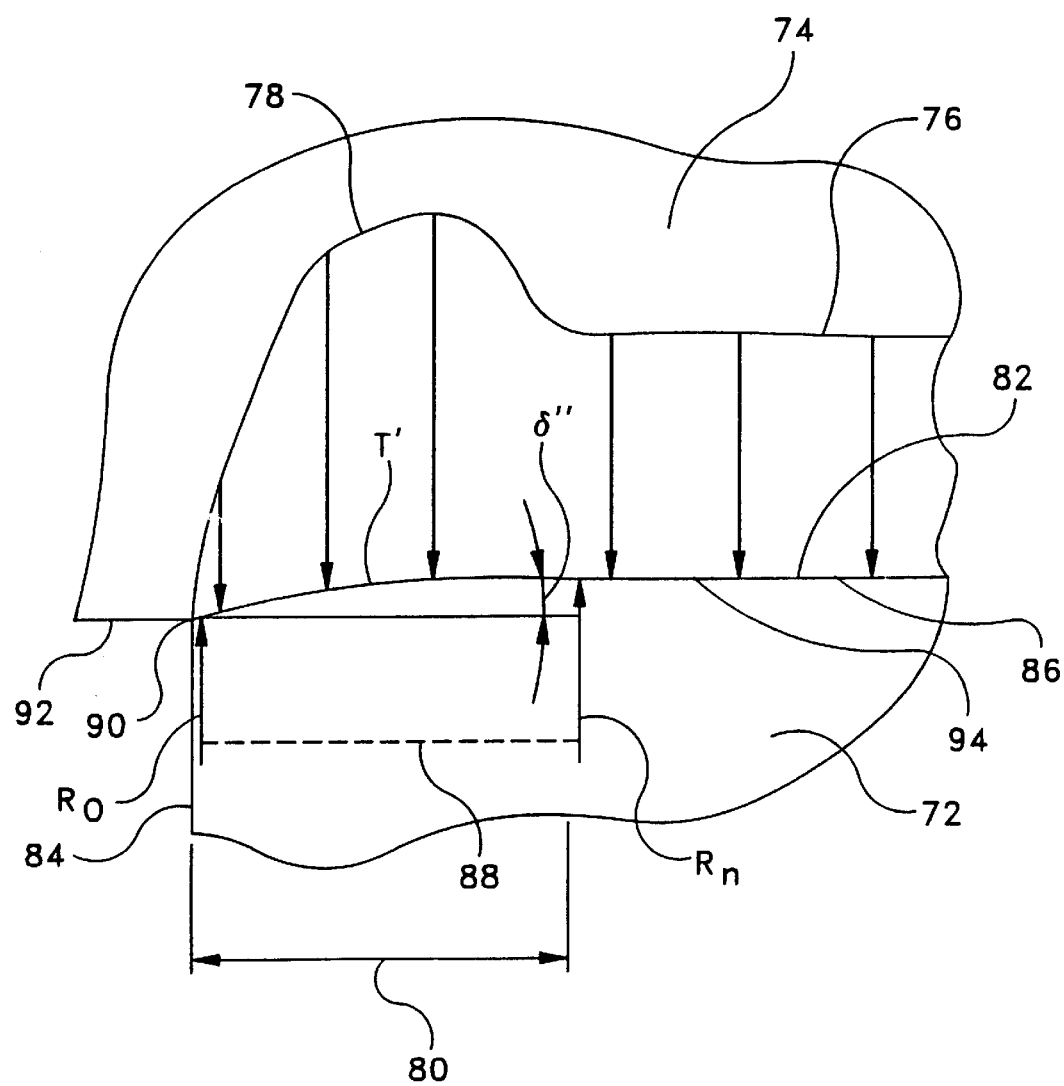
FIG. 9 is an illustration of prosthesis components according to a further embodiment of the present invention useful for further explaining the principles of the present invention.
Figure 10:
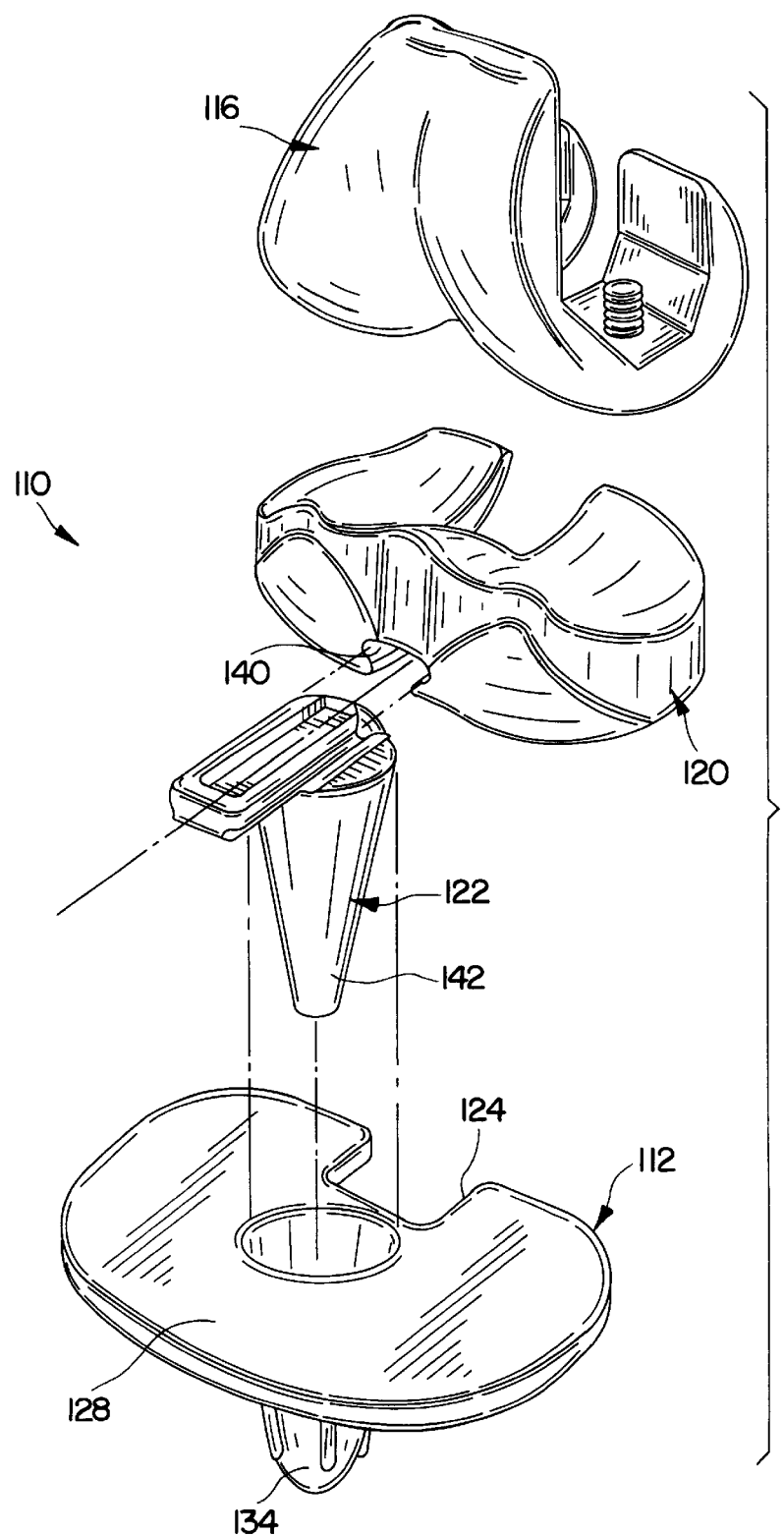
FIG. 10 is an exploded perspective view of a knee prosthesis in accordance with the subject invention.
Figure 11:
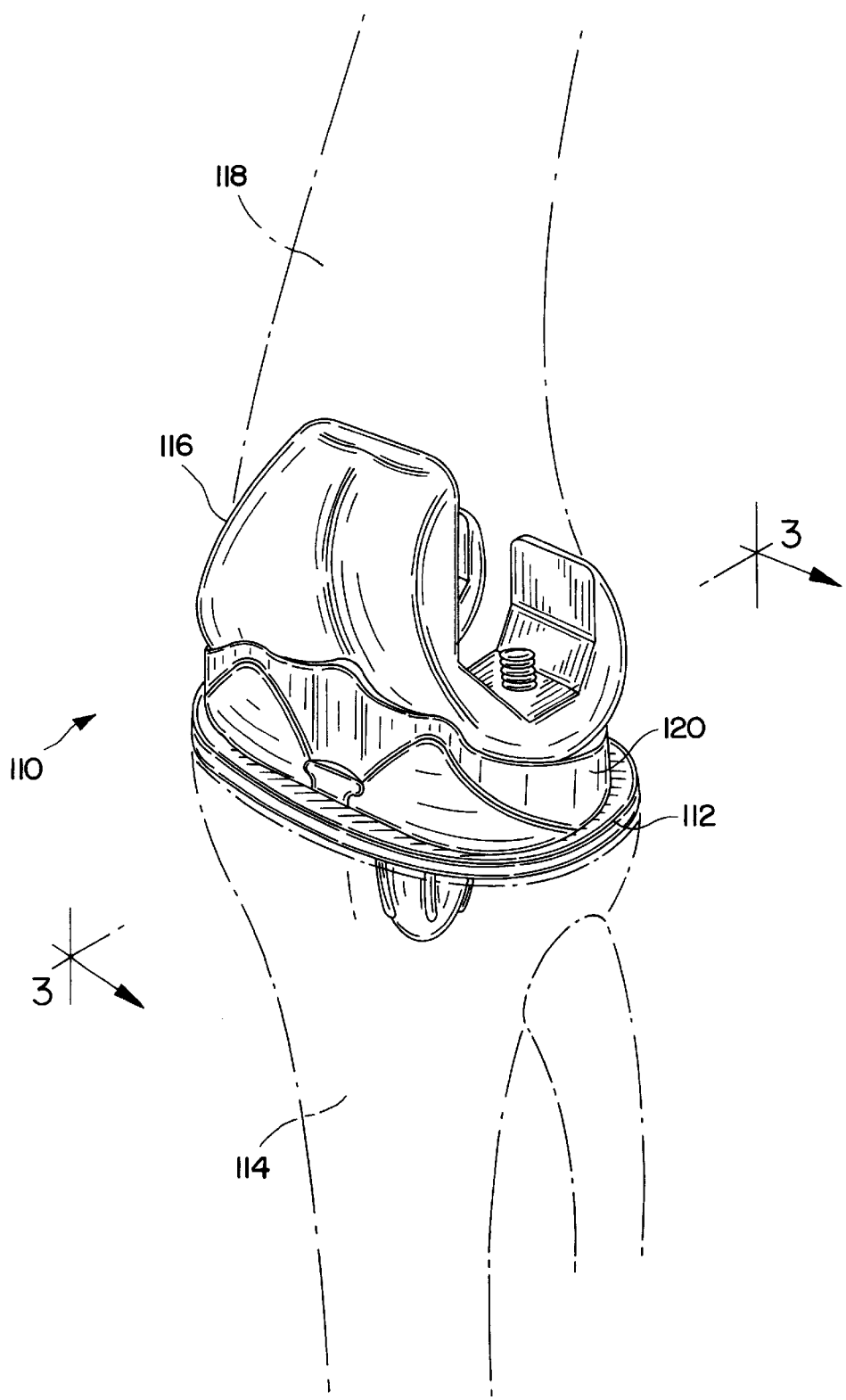
FIG. 11 is a perspective view of the assembled prosthesis shown in FIG. 10.

In FIG. 9, a preferred embodiment of prosthesis component platform 72 is shown in stress contact with a thermoplastic bearing 74. The stress contour is shown by curve 76 having a stress concentration curve portion 78 in region 80. The tapered surface T' merges with the platform 72 planar surface 82 in a radius $R_n$. However the tapered surface T' at platform edge 84, which edge is generally normal to and in contact with surface 86 of bearing 74, has no radius corresponding to radius $R_s$, FIG. 8.

In this embodiment, the surface T' comprises a curvature of a series of contiguous tangentially coupled radii $R_o$ to $R_n$ as represented by dashed line 88. Thus the surface T' blends in with the plane of surface 82 by radius $R_n$ but merges in a relatively sharp corner 90 with edge 84. For practical purposes the corner 90 is broken to remove burrs and to round it somewhat to remove the sharpness thereof in the interest of safety to persons handling the platform 72. Otherwise for purposes of minimizing edge wiping damage, the corner 90 need not have a radius, including the relatively small radius $R_s$ of FIG. 8. Consequently, the load, and thus, the deformation δ", in the softer plastic bearing 74 varies gradually from the edge 84 to the planar portion of surface 82 regardless the presence of an edge radius at corner 90. This results in reduced stress concentration at the edge region in comparison to the high stress concentration with the non-linear and abrupt localized deformation δ (strain) in the prior art arrangement of FIG. 1.

The relatively small radius $R_s$ is not needed because the compressive stress curve portion 78 is reduced in value without that radius. No edge radius on the platform at corner 90 is therefore necessary to minimize the wear at the platform edge 84. The stress concentration at the edge region 80 is reduced as manifested by the gradual change in deformation δ" in region 80 from the bearing surface 92, not in contact with platform surface T'", to interior bearing surface 94 in contact with surface 82.

The stress concentration in region 80 thus increases preferably in this embodiment a maximum of only about 25% as illustrated. This is a significant reduction in stress in the bearing 20 as compared to a 400% edge stress concentration of the prior art bearing arrangement of FIG. 1. While a 25% increase in stress concentration as illustrated in the present embodiment, other values, e.g., up to about 100% increase may be permissible in certain implementations. Since the taper of tapered surface T may be controlled to predetermined requirements, the 25% or even less increase in stress concentration is not a problem to achieve, and the lower the value the better the bearing edge wear performance of a given implementation.

A similar edge wiping configuration is associated with the patellar bearing 48 and patellar platform 50 of the patellar component 18, FIG. 2. Thus the patellar platform 50 surface edge 52 is also tapered with a tapered surface T similar to the tapering of the platform member 23 of FIG. 5.

Figure 6:
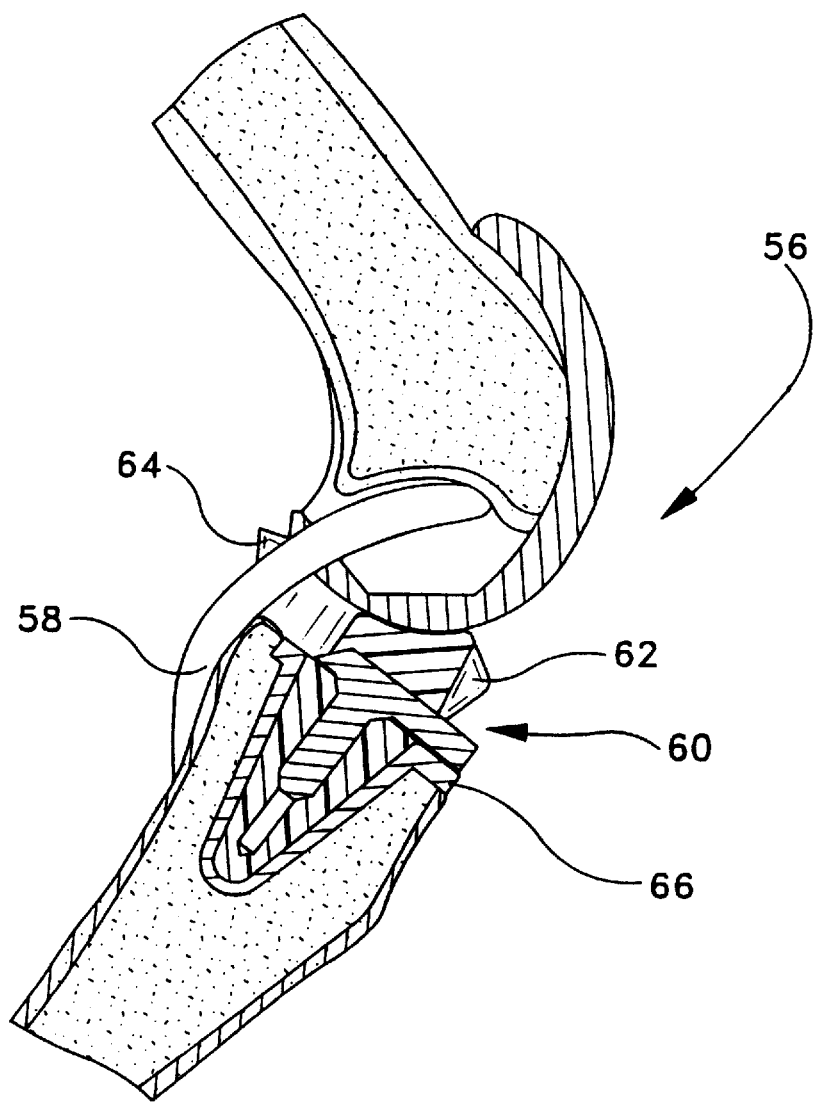
FIG. 6 is a side elevation sectional view of a knee and prosthesis in a second embodiment of the present invention.
Figure 7:
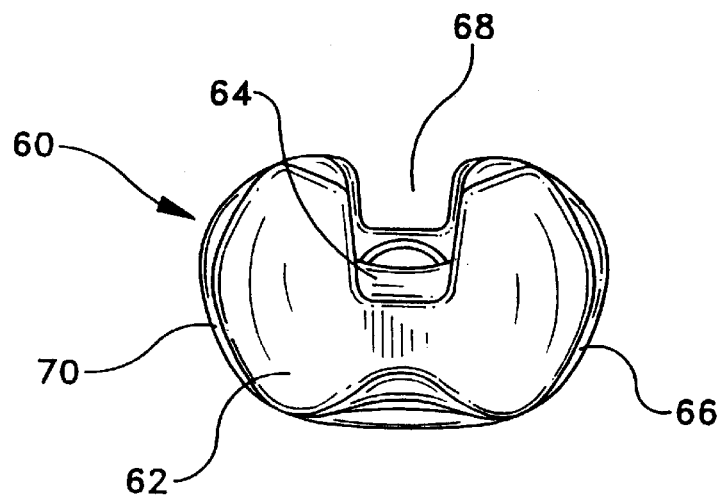
FIG. 7 is a plan view of the tibial bearing and platform components of the prosthesis of FIG. 6.

The edge tapering described has another benefit. The embodiment of the tibial bearing 20 of FIGS. 3 and 4 is intended for use in a knee replacement where the posterior cruciate ligament of the knee 54, FIG. 2, is not retained. Where the posterior cruciate ligament 58 is retained in a knee 56, FIG. 6, an alternate embodiment knee replacement 60, shown in FIGS. 6 and 7, is used. In FIG. 6, a posterior cruciate retaining tibial bearing 62 has a posterior bearing notch 64 to clear the ligament 58. The associated tibial platform notch 68, FIG. 7, to accommodate the ligament 58.

To reduce tibial component inventory in a manufacturing environment, thus reduce costs, it is desirable to use the alternate tibial platform 66 for cases where the posterior cruciate ligament 58 is not retained. Thus it is desirable to use the tibial bearing 20, FIG. 2, with the alternate tibial platform 66, FIG. 6. In such cases, if an alternate tibial platform 66 with a prior art edge 42 as illustrated in FIG. 1 is used, the edge wiping effect of the notch 68, FIG. 7, would produce substantially increased, and unacceptable, wear on the planar tibial bearing 20 surface 28, FIG. 3. The use of an edge 70, FIG. 7, on platform 66 in the notch 68 with a tapered region 44, FIG. 8, will, however, produce only minor, and acceptable, increase in wear. Thus the use of a tapered edge 70 on the platform 66 allows the use of a common tibial platform for both bearing types of FIGS. 2–4, bearing 20 and FIGS. 6 and 7, bearing 62 (the latter with a notch 64) substantially reducing the amount and thus cost of inventory associated with a system for knee replacement. Further, the use of a common tibial platform 66, FIGS. 6 and 7, eliminates the possibility of the wrong platform being used with a particular bearing.

In FIG. 8, the tapered region 44 is a cylindrical surface (where the edge 34 is straight) or a toroidal surface (where the edge 34 is an arc) of width W, where the preferred taper radius $R_t$ of the cross section of the cylinder or toroid is very large compared to the normally used small radius $R_s$ at the platform corner. Finite element analysis of the tapered edge configuration and the prior art edge 42 of FIG. 1 shows a stress magnification of only about 25% for the tapered edge but an almost 400% stress magnification for the prior art edge 42 as discussed above. In most prosthesis designs using articulating bearing and platform surfaces, the peak bearing pressures do not occur at the edge, thus a minor stress increase does not substantially increase overall surface damage. However, a four times increase in stress at the edge will, in most implementations, mean that the stresses at the edge significantly exceed those away from the edge and thus such a magnification will substantially increase overall surface damage.

An alternate knee prosthesis in accordance with the subject invention is identified generally by the numeral 110 in FIGS. 10–13. The prosthesis 110 includes a tibial component 112 for implantation in a resected proximal end of a tibia 114. The prosthesis 110 further includes a femoral component 116 for implantation in a resected distal end of a femur 118. A thermoplastic bearing 120 is disposed between the tibial component 112 and the femoral component 116, and is in articulating bearing engagement with both the tibial and femoral components 112 and 116, substantially as in the prosthetic joint described above and illustrated in FIGS. 2–7. An intermediate element 122 is provided between the tibial component 112 and the bearing 120 for guiding the bearing 120 relative to the tibial component 112 as explained further below.

With reference to FIGS. 12 and 13, the tibial component 112 includes a generally planar platform 124 for engagement against the resected proximal end 114. The platform 124 includes a generally planar superior surface 128 for sliding articulating engagement with the bearing 120. Regions of the bearing surface 128 adjacent edge portions of the tibial platform 124 preferably include the above described stress reducing contact configuration, including a gradually cammed region extending inwardly from the edge.

The tibial component 112 further includes a stem 134 for implantation in the proximal end of the tibia 114. The stem 134 includes a hollow conically generated interior surface 138 which opens to and intersects the bearing surface 128 of the tibial platform 124.

As noted above, the intermediate element 122 is disposed between the tibial component 112 and the bearing 120 to guide movement therebetween. More particularly, the inferior surface of the bearing 120 is formed to include a dove-tailed slot 140 formed therein and extending in an anterior-to-posterior direction. The dove-tailed slot 140 is of uniform cross-sectional shape substantially along its entire length. The intermediate element 122 includes a thermoplastic conical bearing section 142 and a metallic guide section 144. The conical bearing section 142 has a conical external surface configuration generally conforming to the conical interior shape 138 of the stem 134 on the tibial component 112. Thus, the conical bearing section 142 of the intermediate element 122 can freely pivot about its longitudinal axis within the stem 134 of the tibial component 112. The guide section 144 includes a shaft 146 having a knurled portion 148 rigidly secured in the conical bearing section 142. A longitudinal axis of the shaft 142 is coaxial with the axis of the conical bearing section 142. Hence, the shaft 146 will rotate about its axis with the conical bearing section 142 in the conical recess 138 of the stem 134 in the tibial platform 112. The guide section 144 further includes a control arm 150 extending rigidly from the shaft 146. The control arm 150 is of dove-tailed shape compatible with the dove-tailed shape slot 140 in the inferior surface of the bearing 120. Thus, the bearing 120 and the control arm 150 can slide relative to one another. As noted above, the anterior surface of the bearing 120 is in sliding bearing engagement with the superior bearing surface 124 of the tibial component 112. Thus, the control arm 150 of the intermediate component 122 functions to guide this bearing movement in generally anterior-to-posterior directions.

As shown most clearly in FIG. 14, the control arm 150 includes opposed anterior and posterior ends 152 and 154 and dove-tailed shaped side walls 156 extending therebetween. The edge configuration of each side wall 156 in cross-section, as more clearly shown in FIG. 15, defines a two dimensional shaped curve extending between the upper surface 157 and the lower surface 158 of the control arm 150. Each side wall 156 defines a substantial mirror image of the contiguous side wall of the dove-tailed slot 140 of bearing 120. With reference to FIG. 12, the bearing 120 slides to an anteriorly extreme position when the knee is in extension. In this position, the anterior end 152 of the control arm 150 is disposed between the anterior and posterior extremes of the dove-tailed slot 140, and the posterior end 154 of the control arm 150 is disposed posteriorly of the bearing 120. Conversely, as shown in FIG. 13, when the knee is in flexion, the bearing 120 slides to a posterior extreme position. In this condition, the anterior end 152 of the control arm 150 is disposed anteriorly of the bearing 120, and the posterior end 154 of the control arm 150 is intermediate the anterior and posterior extremes of the bearing 120. Thus, as the knee undergoes normal flexion and extension, the edges at the interface of the side surfaces 156 of the control arm 150 and the anterior and posterior ends 152 and 154 wipe over the thermoplastic surfaces defining the dove-tailed slot 140 in the bearing 120. During this articulation, the knee joint is subjected to lateral loads. These lateral loads will generate edge stress concentrations in the plastic bearing 120 in proximity to the anterior and posterior ends 152 and 154 of the control arm 150. The stress concentrations have the potential for causing early failure of the thermoplastic bearing 120. To prevent these problems, the control arm 150 is gradually tapered to a smaller cross-sectional shape at regions adjacent the anterior and posterior ends 152 and 154 thereof. The gradual tapering regions thereof are identified generally by the numerals 162 and 164 in FIG. 14, and extend over distances "w". In the preferred embodiment, each corner region of the side walls 156 of the control arm 150 is generated by sweeping the two dimensional shaped curve of wall 156 along a straight line 167 (see FIG. 14) until the shaped curve 156 is at the distance "w" from the end 152 or 154. At these points, the shaped curve 156 is swept along the curve defined by the respective tapering region 162 or 164, which may be a curve similar to those shown in either FIGS. 8 or 9. Thus, the tapering regions 162 and 164 are of complex, compound curvature.

As in the previous embodiments, the distance "w" over which the gradual taper exists is significantly greater than the maximum relief "δ" achieved by the taper. The angle and shape of the tapered regions 162 and 164 may be comparable to the angle and shape referred to above in connection with the other embodiments of the subject invention, such as the embodiments of FIGS. 8 and 9.

The use of a prosthesis according to the present invention can in most instances substantially eliminate the adverse effect of stress edge wiping, thereby allowing the development and use of improved designs for improved performance and increased range of application. The present invention has wide applicability to the prosthetic art and can be applied to almost all replacement joints now in use including hips, ankles, shoulders, fingers, toes and elbows.

It should be understood that modifications may be made to the disclosed embodiments by one of ordinary skill. The disclosed embodiments are given by way of example and not limitation, the scope of the invention being defined by the appended claims.

What is claimed is:

1. A prosthetic joint comprising: first and second members each having a surface sliding under load and in contact with one another, a combination comprising:

a first member having a first surface; and a second member having a second surface said first and second surfaces sliding under load and in contact with one another, said second surface including an edge, said second surface engaging the first surface in sliding contact such that said first surface and said second surface, including said edge thereof, are under compressive load during said sliding contact, said compressive load causing portions of said first member in engagement with the second member to exhibit a contact stress of at least a first value, said second surface having a gradual convex tapering region extending inwardly on said second surface from said edge a selected distance so as to cause the first member to exhibit an increased edge contact stress concentration in portions of the first member in engagement with the tapering region of the second member, said increased edge contact stress being of a second value which is no more than about twice said first value.

2. The combination of claim 1, wherein the second member is metal and the first member is a thermoplastic.

3. The combination of claim 1, wherein the first member is of a lower hardness than the second member.

4. The combination of claim 1, wherein the second surface at said gradual tapering region comprises a curvature which is tangential to said second surface interiorly of said tapering region.

5. The combination of claim 1, wherein the second surface at said gradual tapering region comprises a curvature of a plurality of contiguous tangential curves of differing radii.

6. The combination of claim 1, wherein the tapered region approximates a radius of greater than 25 mm and extends inwardly from the edge an extent of at least about 2.5 mm.

7. The combination of claim 6, wherein the tapered region approximates a radius of at least about 50 mm and extends inwardly from the edge of an extent of at least about 3.0 mm.

8. The combination of claim 1, wherein the tapered region terminates at said edge in a curved corner of radius $R_s$, said tapered region approximating a radius $R_t$, $R_t$ being substantially larger than $R_s$.

9. In a prosthesis including a joint comprising first and second members each having a surface thereof articulating under load in contact with one another, a combination comprising:

a first member having a first surface; and a second member harder than the first member and having a second surface for engaging in articulating contact the first surface, the second surface having an edge, said second surface including said edge being under compressive load with the first surface during said articulating contact, said compressive load causing said first member in the region of said first surface to exhibit a contact stress concentration, said second surface having a gradual tapering region adjacent to and extending inwardly on said second surface a minimum distance W from said edge so as to cause the second member to exhibit a gradual tapering deformation angle α less than 10° with portions of the second surface inwardly from the gradual tapering region.

10. The combination of claim 9, wherein W is at least 2 mm.

11. The combination of claim 9, wherein α is less than 5° and W is at least 3 mm.

12. In a prosthesis including a joint comprising first and second surfaces in sliding load contact with one another, a combination comprising:

a thermoplastic bearing having a planar first surface with a dove-tailed slot formed therein, said dove-tailed slot being of uniform cross-sectional shape entirely therealong; and a control arm having opposed anterior and posterior ends and a cross-sectional shape therebetween for slidable engagement of said control arm in said dove-tailed slot, portions of said control arm between said anterior and posterior ends being under compressive load with portions of said bearing defining the dove-tailed slot, said compressive load causing said bearing in regions of said dove-tailed slot to exhibit a contact stress concentration, portions of said control arm extending inwardly a distance "W" from said anterior and posterior ends being gradually tapered to smaller cross-sectional dimensions so as to exhibit a gradual tapering deformation angle α less than 10° with portions of the control arm inwardly from the tapered portions.

13. The combination of claim 12, wherein the bearing is UHMWPe and the control arm is metal.

14. The combination of claim 12, wherein α is less than 5° and wherein W is at least 3 mm.

15. In a prosthesis including a joint having a combination of first and second members each having a surface thereof articulating under load in contact with one another, the combination comprising:

a first member having a first surface, said first surface having a curved edge configuration as viewed along a first axis, said first surface defining at least one edge as viewed along a second axis, said second axis being perpendicular to said first axis; and a second member having a second surface for engaging in mating, sliding contact with said first surface, said second surface extending from an end of said second member, said second surface defining a substantially mirror-image surface configuration of said first surface as viewed along said first axis, a portion of said second surface defining at least one edge as viewed along said second axis, said second surface engaging said first surface in sliding contact such that said first surface and said second surface are under compressive load during sliding contact, said compressive load causing portions of said first member in engagement with said second member to exhibit a contact stress of a first value, said second surface having a tapering region extending between said edge portion and said end, said tapering region being defined by the sweeping of said curved edge configuration partially about at least one reference axis which is parallel to said second axis, such that said tapering region has a compound curve configuration relative to said first and second axes, and whereby said tapering region causes said first member to exhibit a second value of increased edge contact stress concentration in portions of said first member in engagement with said tapering region of said second member greater than said first value, but less than the edge contact stress concentration which would exist without said tapering region of the second member.

16. The combination of claim 15, wherein said first member is made of thermoplastic material, and wherein said second member is made of a metallic material.

17. The combination of claim 15, wherein said increased edge contact stress is at a second value which is no more than about twice said first value.

18. The combination of claim 15, wherein said prosthesis is a knee prosthesis, and said first member is a bearing, and said second member is a control arm of an intermediate element, said control arm being slidably received in said bearing.

19. The combination of claim 15, wherein said one edge of said first member and said at least one edge of the second member are straight as viewed along said second axis.

20. In a prosthesis including a joint having a combination of first and second surfaces in sliding contact with one another, the combination comprising:

a thermoplastic bearing having a first surface with a dove-tailed, elongated slot formed therein, said dove-tailed slot being of uniform cross-sectional shape; and an elongated, metallic control arm having opposed anterior and posterior ends and a cross-sectional shape therebetween for slidable engagement with said dove-tailed slot, portions of said control arm between said anterior and posterior ends being under compressive load with said bearing, said compressive load causing said bearing to exhibit a contact stress concentration of a first value, said control arm having tapering regions adjacent said anterior and posterior ends, said tapering regions each defining a convex, compound configuration as viewed along an axis perpendicular to the longitudinal axis of said control arm, whereby said tapering regions cause said bearing to exhibit increased edge contact stress concentrations of a second value which is greater than said first value in portions of the bearing in engagement with the tapering regions of said control arm, but which second value is less than the edge contact stress concentrations which would exist without said tapering regions.

21. In a prosthesis including a joint having a combination of first and second members each having a surface thereof articulating under load in contact with one another, the combination comprising:

a first member having a first surface, said first surface having a curved edge configuration as viewed along a first axis; and a second member having a second surface for engaging in mating, sliding contact with said first surface, said second surface extending from an end of said second member, said second surface defining a substantially mirror-image surface configuration of said first surface as viewed along said first axis, said second surface engaging said first surface in sliding contact such that said first surface and said second surface are under compressive load during sliding contact, said compressive load causing portions of said first member in engagement with said second member to exhibit a contact stress of a first value, said second surface having a tapered region extending inwardly a selected distance from said end of the second member so as to cause the first member to exhibit an increased edge contact stress concentration in the portions thereof in engagement with said tapered region of the second member, said increased edge contact stress being of a second value which is greater than said first value but less than the edge contact stress which would exist without said tapered region of the second member.

22. The combination of claim 21, wherein said increased edge contact stress is at a second value which is no more than about twice said first value.

23. The combination of claim 21, wherein said first member is made of thermoplastic material, and wherein said second member is made of a metallic material.

24. The combination of claim 21, wherein said prosthesis is a knee prosthesis, and said first member is a bearing, and said second member is a control arm of an intermediate element, said control arm being slidably received in said bearing.

* * * * *